United States Patent
Smith et al.

[11] Patent Number: 5,191,363
[45] Date of Patent: Mar. 2, 1993

[54] SPORTS GLASSES WITH WATERTIGHT SEAL

[76] Inventors: Terry L. Smith; Diana M. Smith, both of 1706 Barlow La., Sebastopol, Calif. 95472

[21] Appl. No.: 622,007

[22] Filed: Dec. 4, 1990

[51] Int. Cl.$^5$ .............................................. G02C 11/08
[52] U.S. Cl. ...................................... 351/62; 351/43; 351/156
[58] Field of Search .................... 351/43, 62, 156, 157, 351/158

[56] References Cited

U.S. PATENT DOCUMENTS

| | | | |
|---|---|---|---|
| 3,672,750 | 6/1972 | Hagen | 351/43 |
| 4,264,987 | 5/1981 | Runckel | 2/428 |
| 4,405,212 | 9/1983 | Cooper | 351/43 |
| 4,689,837 | 9/1987 | Bollé | 2/440 |
| 4,689,838 | 9/1987 | Angermann et al. | 2/441 |
| 4,755,040 | 7/1988 | Hasibeck | 351/43 |
| 4,818,094 | 4/1989 | Lyons | 351/157 |
| 4,881,803 | 11/1989 | Giles et al. | 351/156 |

*Primary Examiner*—Bruce Y. Arnold
*Assistant Examiner*—Hung Xuan Dang

[57] ABSTRACT

Improved eyewear having a single lens (22) supported by a frame (20) which has temples (26) attached to either side by hinges (24). A wrap-around configuration of the frame and lens essentially hides a single circumferential frame to face water impermeable seal assembly (32) comprising a foam rubber layer (34) overlying a deflatable bladder (36). The inner side of the seal is contoured to fit against the human face and the outer side of the seal is contoured to fit within the frame and lens. Extending from the temples are adjustable retaining means (41) comprising two elongated tubular members (40) with open ends formed of a flexible resilient material, being adjusted by a releasable friction catch (44) to prevent the catch from becoming separated from the tubular members. Tubing (38) connects the bladder (36) and interior portions of the glasses to air removal means which can take the form of a mouthpiece (52) or pump (78) placed at the end of the retaining means or attached to the temple ends (30). Air removal means allow the wearer to deflate or inflate the bladder, and to remove air from the interior portion of the glasses, creating a slight vacuum and a better watertight seal with the face.

20 Claims, 3 Drawing Sheets

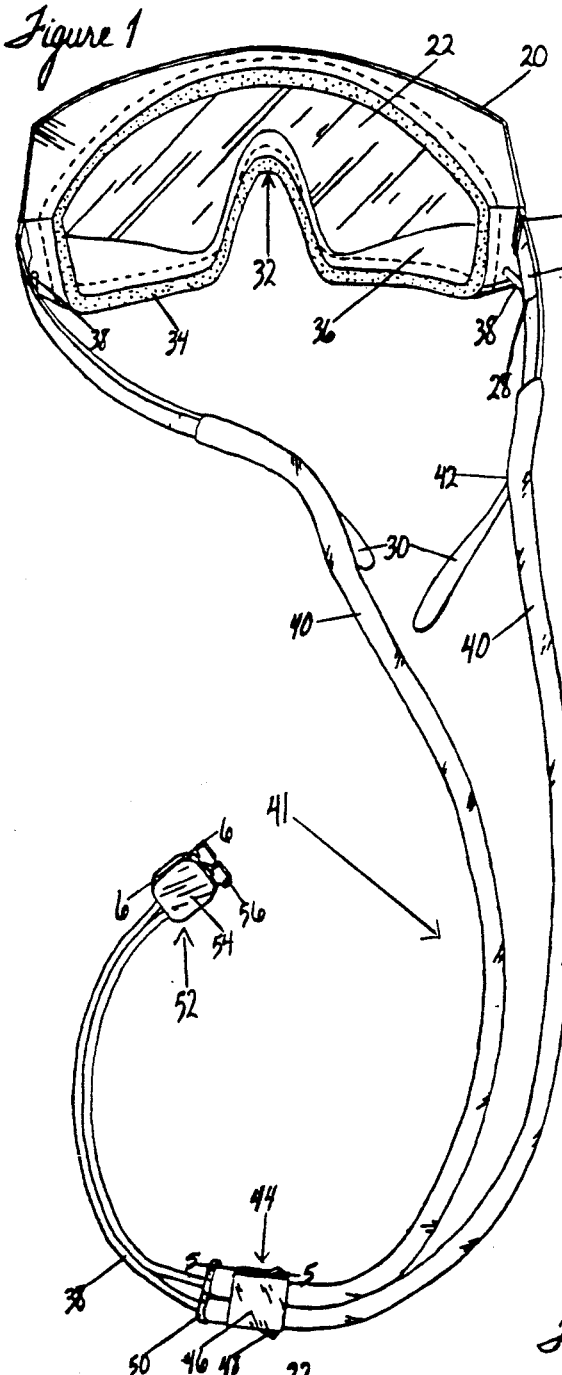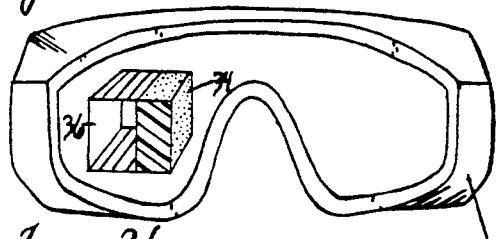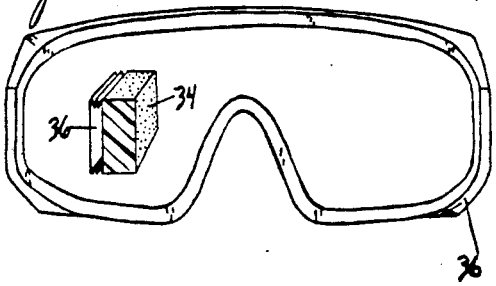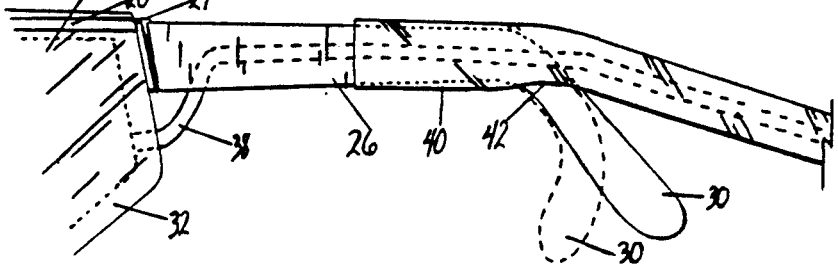

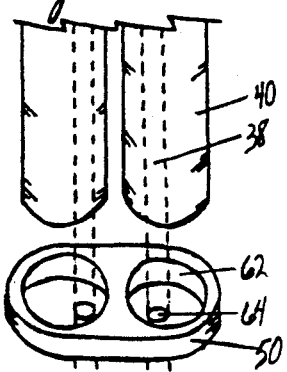
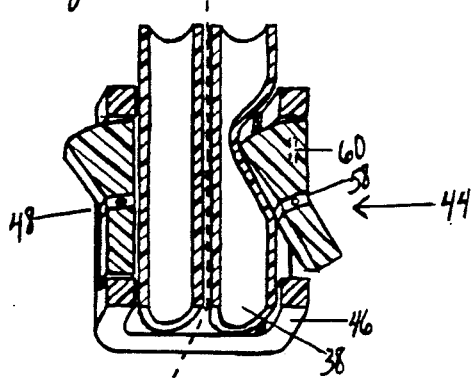
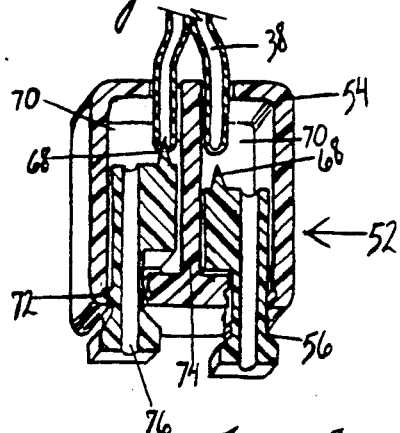
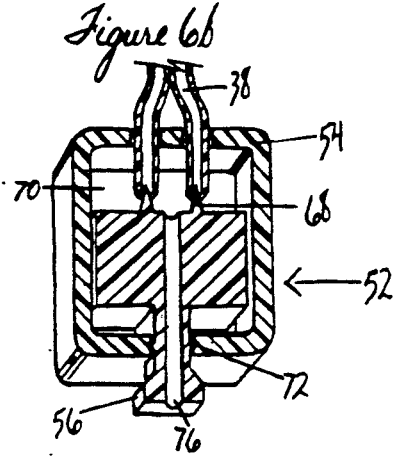
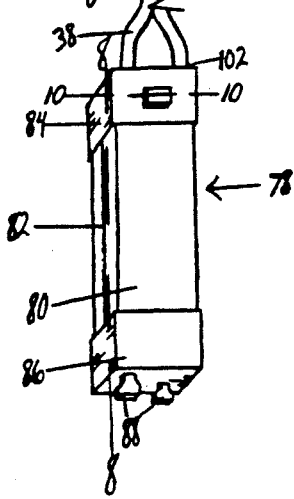
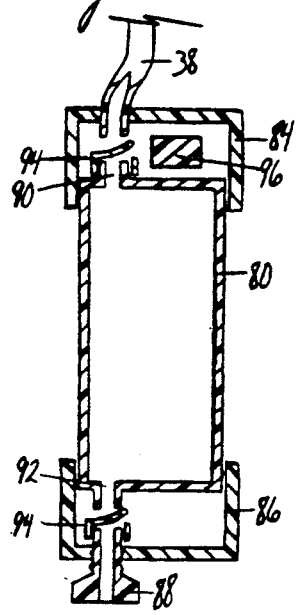
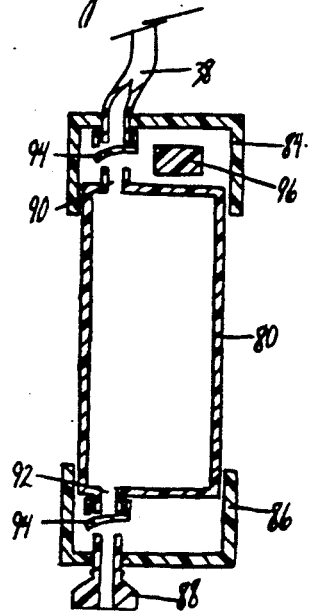

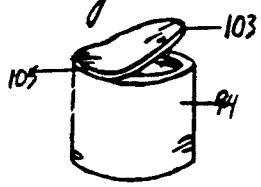
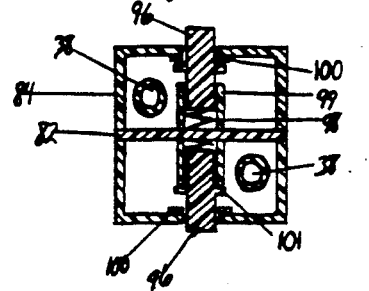
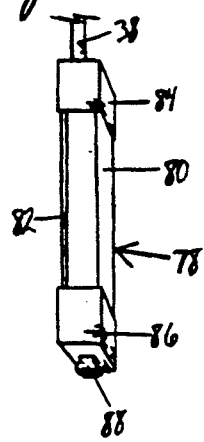
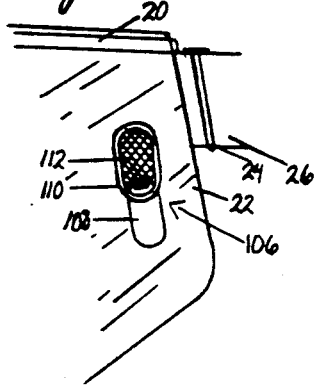
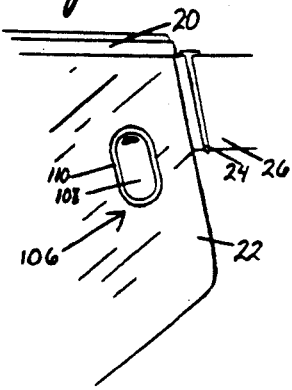
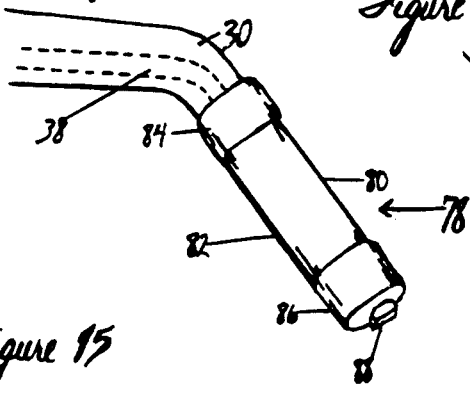
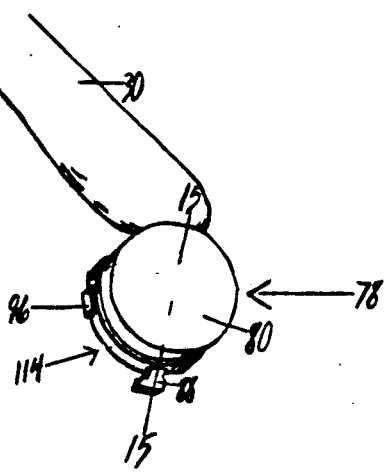
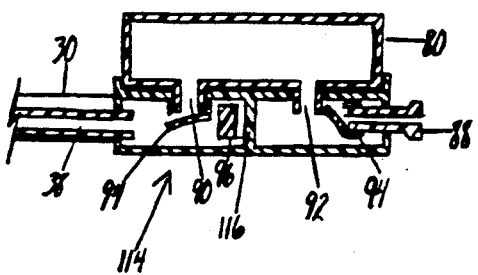

SPORTS GLASSES WITH WATERTIGHT SEAL

BACKGROUND—FIELD OF INVENTION

This invention relates to protective eyewear, specifically to that which is worn in various athletic activities.

BACKGROUND—DESCRIPTION OF PRIOR ART

Participants in outdoor sporting activities often find a need to employ some form of eye protection. The need to protect the eyes and contact lenses from sun, wind, dirt, chlorinated water, salt water and other hazards has prompted the invention of many types of sunglasses and goggles.

While sunglasses can filter the sun's harmful rays, and are extremely desirable and popular for comfort and aesthetic reasons, they cannot efficiently block other damaging elements from entering the eyes of the wearer. Further, sunglasses are not functional in water activities so that the eyes are often left totally unprotected during participation in these activities.

Many types of goggles designed for use in specific activities perform the function of protecting the eyes of the wearer. However, they are limited in their field of use e.g. ski goggles cannot be worn for surfing, etc. A person needing goggles for many different activities has little choice but to purchase a separate pair for each activity. They are rarely worn for other than the purpose for which they were designed if not simply because of their lack of aesthetic appeal.

Cooper U.S. Pat. No. 4,405,212 (1983) shows eyewear that can be used as an every-day spectacle, as a safety goggle, as a watertight swimming goggle and as an underwater diver's mask. In order to be used for these varying functions, appropriate accessories must be used and interchanged to fit the activity. Such changes are time consuming and bothersome with accessories that would tend to get lost. The use of so many accessories would add to the cost of manufacturing, and in time the mating surfaces would wear out, causing a loss of integrity in the watertight capabilities of the glasses. In addition, the glasses are bulky and unattractive with a wide frame and limited lens area.

Hasibeck, U.S. Pat. No. 4,755,040 (1988) shows improved swim goggles. These, like most swim goggles protect the eyes from salt water or chlorinated water and allow the wearer to see clearly underwater. However, they do not offer protection from the sun's harmful rays and they lack aesthetic appeal for every day wear.

Goggles designed for skiing are shown by Angermann et al. U.S. Pat. No. 4,689,838 (1987). These offer the advantage of interchangeable, tinted lens, but like most ski goggles, are limited in their use to skiing and perhaps snowmobiling. They cannot be worn in water activities and are too bulky to be desirable to fashion-conscious consumers. The interchangeable lenses have a tendency to become separated and lost.

Since goggles are designed for use in specific sports and because of their general lack of aesthetic appeal, eyewear must be provided that can be used in a multitude of activities to provide protection for the eyes. This is especially necessary for contact lens wearers. They experience limitations in their ability to participate in many activities simply because of the characteristics of contacts. Contact lenses have a tendency to dry out, pop out, get dirt lodged in them, get washed out during water activities, etc. Contact wearers, are unable to find a single pair of attractive eyewear that would free them to participate in a multitude of activities. Currently, they must stop to remove and store their contact lenses, thereby suffering inconvenience and impairment of vision, or they must avoid such activities entirely.

OBJECTS AND ADVANTAGES

Accordingly, several objects and advantages of the present invention are:

(a) to provide protection for the eyes from hazards such as sand, wind, dust, dirt, salt water, chlorinated water and others which are commonly present where sports are participated in;

(b) to provide eye protection wherein a single pair of glasses can be worn during participation in many activities, including: beach volleyball, swimming, sailing, waterskiing, windsurfing, snowskiing, sandlot football, jet skiing, snowmobiling, canoeing bicycling and more;

(c) to provide protective eyewear that is appealing to a wide variety of wearers for aesthetic as well as functional reasons;

(d) to provide means whereby the contact lens wearer is free to participate in a wide variety of activities without the threat of contact loss or damage, or eye discomfort;

(e) to provide a fit that can be easily tailored by the wearer to fit his individual face shape and needs;

(f) to eliminate the need for an individual to own a pair of sunglasses or goggles for each activity he participates in;

(g) to provide versatile eyeglass retaining means with a catch that cannot slide off and become lost;

(h) to provide an air and water tight seal with the wearer's face if such a seal is desired for water activities where the head may be submerged;

(i) to provide means whereby the eyewear can be worn as sunglasses for everyday use;

(j) to protect the eyes from the harmful rays of the sun, especially in the water where those effects are multiplied;

(k) to allow the wearer to see clearly under water;

(l) to provide a seal assembly that is not immediately noticeable to the casual observer;

(m) to provide a secure seal with the face that is easily achieved;

(n) to provide versatile eye protection that is self-contained, eliminating the need to carry extra parts for interchanging.

Further objects and advantages will become apparent from a consideration of the ensuing description and drawings.

DRAWING FIGURES

In the drawings, closely related figures have the same number but different alphabetic suffixes.

FIG. 1 shows a comprehensive view of the eyewear from the above-rear.

FIG. 2a shows the bladder in its inflated state.

FIG. 2b shows the bladder in its deflated state.

FIG. 3 shows a side view of the glasses, describing the path of the tubing.

FIG. 4 shows the stop and possible helical configuration of the tubing.

FIG. 5 is a cross-sectional view of the releasable friction catch, taken along line 5—5 of FIG. 1.

FIG. 6a is a cross-sectional view of a mouthpiece with two inner chambers, taken along line 6—6 of FIG. 1.

FIG. 6b is a cross sectional view of a mouthpiece with a single inner chamber, taken along line 6—6 of FIG. 1.

FIG. 7 shows a top-side view of the optional pump.

FIG. 8a shows a cross sectional view of the pump allowing directional flow of air towards the bladder, taken along line 8—8 of FIG. 7.

FIG. 8b shows a cross sectional view of the pump allowing directional flow of air away from the interior of the glasses, taken along line 8—8 of FIG. 7.

FIG. 9 shows a valve.

FIG. 10 shows a cross sectional view of the release button, taken along line 10—10 of FIG. 7.

FIG. 11 shows a side view of a pump with a single function.

FIG. 12a shows an optional air vent, open.

FIG. 12b shows an optional air vent, closed.

FIG. 13 shows optional placement of pump mechanism on temple end.

FIG. 14 shows a round version of a pump attached to a temple end.

FIG. 15 shows a cross-sectional view of a round pump, taken along line 15—15 of FIG. 14.

| Reference Numerals in Drawings | |
|---|---|
| 20 frame | 22 lens |
| 24 hinge | 26 temple |
| 28 hole in temple | 30 temple end |
| 32 seal assembly | 34 foam rubber |
| 36 bladder | 38 tubing |
| 40 tubular member | 41 adjustable retaining means |
| 42 hole in tubular member | 44 releasable friction catch |
| 46 casing of catch | 48 rocking switch |
| 50 stop | 53 mouthpiece |
| 54 mouthpiece casing | 56 pointed member |
| 58 hinge of catch | 60 snap on switch |
| 62 stop-holes for 40 | 64 stop-holes for 38 |
| 66 helical molding | 68 pointed member |
| 70 chamber | 72 snap |
| 74 partition | 76 hollow channel in plug |
| 78 pump | 80 deformable air chamber |
| 82 partition/base | 84 top casing |
| 86 bottom casing | 88 extension |
| 90 top stem | 92 bottom stem |
| 94 valve | 96 release button |
| 98 spring | 99 release button channel |
| 100 release button seal | 101 release button projection |
| 102 top casing holes for tubing | 103 flap |
| 104 bottom casing holes for stems (88) | |
| 105 attachment point | 106 vent |
| 108 cover | 110 channel |
| 112 screen | 114 base |
| 116 partition in round pump | |

DESCRIPTION FIGS. 1–15

A typical embodiment of the eyewear of the present invention is illustrated in FIG. 1. Wrap-around style sunglasses have a flexible frame 20 that holds a lens 22, preferably polarized, tinted, or coated with material to filter the sun's harmful rays. Said lens may be multi-layered for insulation purposes if desired but for simplicity is shown as a single layer. A Hinge 24 attaches the frame to a hollow temple 26 on either side of the glasses. The wrap-around configuration of the lens essentially hides a single circumferential frame-to-face water impermeable seal assembly 32. This seal consists of a foam rubber layer 34 overlying a deflatable bladder 36. The inner side of the seal is contoured to fit against the human face to comfortably conform over the eyes and about the nose. The outer side of the seal is contoured to fit within the frame and lens.

Hollow tubing 38 extends from the interior portion of the glasses through the bladder and enters a temple 26 through hole 28 which is spaced far enough from hinge 24 to allow the hinge to bend freely. The tubing then passes through adjustable retaining means 41, exits at stop 50 and extends to the mouthpiece 52. Adjustable retaining means include two elongated tubular members 40 formed of a flexible, resilient material, having open ends. One tube slips over each temple end 30 and is held there by friction. The temple end exits tubular member at hole 42 for comfort and to allow for adjustment e.g. bending of the temple ends.

A releasable friction catch 44 slides over the tubular members to allow for adjustment. The catch contains a locking switch 48 contained by a casing 46. The tubular members terminate at a stop 50. Tubing 38 continues and terminates at a mouthpiece 52 which consists of a casing 54 and one or more plugs 56 in inner chambers.

FIG. 2a shows a bladder 36 in its inflated state with a cross-section shown inside. FIG. 2b shows the deflated state. FIG. 3 is a side view of the glasses of the invention, showing the passage of the tubing. The open end of the tubing is flush with the interior, flat surface of the seal assembly. Tubing exits the temple and enters a tubular member 40 at a point opposite hole 42. Temple end 30 is made of materials that allow it to bend and retain a cable temple shape if it is desired. A flexible metal base coated in a flexible plastic can be used to accomplish this purpose.

FIG. 4 shows details of a stop 50. The end of a tubular member 40 is fixed e.g. glued into a hole 62. Each tube 38 passes through a hole 64. The tubing can be formed into an optional helical configuration 66 to reduce total length. FIG. 5 shows a cross-sectional view of a releasable friction catch 44. When in an open position, shown on the left, a rocking switch 48 allows the catch to slide up and down the tubular members for adjustment purposes. The switch turns on a hinge 58 and can be snapped in a closed position, shown on the right side, and held there by a snap approximately positioned at point 60.

FIG. 6a is a cross-sectional view of a mouthpiece 52 taken along line 6—6 of FIG. 1. Tubing 38 enters the mouthpiece through spaced holes in the top of a casing 54. A partition 74 divides the mouthpiece into two individual chambers 70. When closed, as shown on the left side, the end of the tubing is sealed by a pointed member 68 which extends from the upper end of the plug. The plug has a hollow channel 76 and is held in a closed position by a snap 72. FIG. 6b shows an optional mouthpiece for use in glasses that don't have a bladder in the seal assembly, or if means for removing air from the interior portion of the glasses is not desired. It consists of a casing 54, a single chamber 70, and a single plug 56 with two pointed members 68, a hollow channel 76 in the center and a snap 72.

DESCRIPTION OF PUMP

FIG. 7 shows a top-side view of an optional pump 78. Tubing 38 coming from the glasses enters a top pump casing 84 at holes 102. A deformable air chamber 80 is attached on either side of a partition/base 82. Casings 84 and 86 fit over the ends of this assembly with extensions 88 extending out of the bottom casing. FIG. 8a shows a cut-away view of front of pump 78, showing detail of the inner workings. Directional flow of air towards glasses to inflate the bladder 36 is accomplished by use of valves 94 which are fixed (e.g. glued) over a stem 90 on the upper end of a deformable air chamber 80 and the portion of an extension 88 which is inside a bottom casing 86. FIG. 8b is identical to FIG. 8a except that it allows directional flow of air away from glasses to create a slight vacuum in the interior of the glasses. Valves 94 are fixed (e.g. glued) over the end of a tube 38 and a stem 92 extending from the bottom of a deformable air chamber 80. Tubes, stems, and the inner end of the extension are essentially the same diameter so that only one size of valve is needed. The extension snaps in to hold the lower valve closed.

FIG. 9 shows a valve 94. It is formed of a flexible, resilient material, e.g. rubber. The bottom end remains open to fit over tube ends, stems, or inner ends of extensions. The top end is covered by a flap 103 that is attached to the top end of the valve at attachment point 105. FIG. 10 shows a cross-sectional view of the release button taken along 10—10 of FIG. 7. It is held in a closed position by a spring 98 that reaches from the underside of the button to a portion of the partition/base directly below it. A seal 100 on the inside of the casing or upper side of the button seals the area between the button and casing. FIG. 11 shows a pump 78 with only one deformable air chamber 80.

FIGS. 12a and 12b show an optional vent 106 placed on the sides of the glasses. It has a cover 108 that slides in a rubber channel 110. The fit between the cover and channel is tight enough to seal when the vent is closed, as shown in FIG. 12b. A screen 112 covers the underside of the vent, seen in FIG. 12a where the vent is open.

FIG. 13 shows an optional placement of a pump 78 on a temple end 30. This pump is placed on either or both temple ends. To accommodate this pump, the temple end must be slightly larger than average.

FIG. 14 shows a round version of a pump 78 attached to a temple end 30. It is similar in structure to the previously described pump, but has a deformable air chamber 80 on top of a base 114. This pump can take a number of shapes, including round, hexagonal, square, triangular, etc. A release button 96 is placed on the side of the upper half of the base. As seen in FIG. 15, this base is divided by a partition 116. Stems 90 and 92 extend from the underside of a deformable air chamber 80. Extension 88 extends from the bottom of this pump and can be snapped in to close the lower valve and prevent accidental compression of the deformable air chamber.

OPERATION OF INVENTION

The eyewear of the invention are worn like common sunglasses. A single lens 22 is worn in front of the eyes and extends back on either side to allow the wearer a wide field of vision. The lens is preferably tinted and/or coated with material to filter the sun's harmful rays. This particular shape of lens covers a seal assembly 32 which can be seen only from the rear, extreme above and below when the glasses are positioned on the wearer's face. The lens and seal assembly is supported by temples that are attached to the frame on either side as is common.

By using the releasable friction catch the glasses may be held in any desired position from dangling around the wearer's neck to snugly against the wearer's head and face. The catch holds the retaining means in the desired position when switches 48 are snapped in a closed position. When the switches are in an open position, the catch can be moved up and down the retaining means for adjustment purposes. A stop 50 serves the purpose of preventing accidental disassembly of the retaining means by the wearer.

A bladder as part of the seal assembly adds versatility to the glasses. The bladder is deflated when the wearer pulls the plug out to unstop the end of the tubing. He then "sucks" air from the plug which is located on the side of the mouthpiece that is connected to the bladder by tubing. When the bladder is deflated, the glasses may be worn as regular sunglasses, because the foam layer is pulled away from the wearer's face, allowing for circulation of air and comfort. When the bladder is inflated by blowing air into the appropriate plug, the foam contacts the wearer's face, blocking out wind, dust, sand, snow, etc. The bladder can be inflated to various levels to allow for the differences in shapes of human faces and to fit the wearer's needs at a particular time. In addition, when the bladder 36 is inflated, a seal can be created to prevent the ingress of water for swimming and other water activities when the wearer's head might become submerged. This seal is created by pulling the glasses snuggly against the wearer's face by using the releasable friction catch to tighten the retaining means. Then air is removed from the interior portion of the glasses, creating a slight vacuum, by "sucking" on the appropriate plug. When the plug is pushed in, the end of the tube is plugged to prevent the loss of desired air pressure. A snap 54 holds the plug in a locked closed position. A seal might also be achieved by simply tightening the retaining means, then pressing the glasses towards the face to create a slight vacuum.

OPERATION OF PUMP

An optional pump 78 can be used to create desired air pressure in the bladder or in the interior of the glasses. The wearer pulls an extension 99 out to allow the bottom valve to operate. Flap 103 on valve 94 is flexible to open when pushed against by air flow, then close again when air flow is stopped. He then applies pressure to a deformable air chamber. The temporary deformation caused by this pressure forces air out of the chamber. When the wearer removes pressure from the air chamber, it is refilled with air. This process is repeated until the desired pressure is achieved. The extension is then snapped in to close the valve and prevent accidental compression of the air chamber. Extension 88 also allows the pump to be bypassed so that the wearer can "suck" or "blow" air as desired. Like plugs 56 of the mouthpiece 52, the extensions can be snapped in. This closes the lower valve and prevents accidental compression of either or both deformable air chambers. This also allows the wearer to use only one side of the pump at a time. Depression of a release button 96 allows a release of the air pressure in the bladder and/or the vacuum in the interior of the glasses.

An optional vent 106 can be opened to allow air flow to the interior portion of the glasses. A screen 112 on the underside of the vent prevent sand, snowflakes, etc from entering the glasses, but allows air flow to decrease fogging of the lens. A cover 108 slides in a channel 110 to close the vent. The fit between the cover and channel must be watertight.

The pump shown in FIG. 11 would be used in glasses without a bladder, or if means for removing air from the interior portion of the glasses is not desired. When placed on a temple end, as shown in FIG. 13, the operation of pump 78 is similar to that of the pump shown in FIG. 11. A differently shaped pump could be attached to the temple end as shown in FIG. 14. Although shown with an immovable attachment, this pump could be attached by a springed hinge that would press the pump towards the wearer's head for added security in holding the glasses in place. Valve placement determines the direction of air flow. The pump shown in FIG. 15 allows air to be pumped toward the glasses. To allow air to be pumped away from the glasses, a valve 94 would be placed over bottom stem 92 and the end of tubing 38.

SUMMARY, RAMIFICATIONS, AND SCOPE

Accordingly, the reader will see that the eyewear of this invention can be worn for participation in a variety of sports, eliminating the need for a different pair of goggles or sunglasses for each activity. In addition, they allow the contact lens wearer to participate in many sports without fear of contact loss or damage. Some further, more specific advantages include:

they provide protection for the eyes form the sun's harmful rays;

they protect the eyes from drying wind, sand and other materials that are damaging to the eyes;

they can be used to provide an environment sealed against water, especially salt water and chlorinated water in swimming and other water activities;

they allow the wearer to see clearly under water;

they provide a fit that can be easily tailored to an individuals face shape and needs;

they can be worn as everyday sunglasses;

they look very much like the wrap-around sunglasses that are presently popular;

the temples can be bent and retain a cable temple shape to hold the glasses more securely against the wearer's face;

they provide a seal assembly that is not immediately apparent to the casual observer;

they can be adjusted to allow ventilation which prevents fogging of the lens;

they can be worn for participation in a variety of activities, including skiing, water activities and beach activities.

Although the description above contains many specificities, these should not be construed as limiting the scope of the invention but as merely providing illustrations of some of the presently preferred embodiments of this invention. For example, the glasses may be provided with two lenses instead of one; the bladder may be eliminated, the seal assembly being made only of foam' the retaining means may take a variety of shapes, such as round, square, rectangular, oval, etc.; the lens can be coated with a variety of materials for polarization or UV filtering; the lens can take a variety of shapes and colors; the catch can have a single switch on top; etc.

Thus, the scope of the invention should be determined by the appended claims and their legal equivilants, rather than by the examples given.

We claim:

1. Improved eyewear for protecting the eyes of a wearer during participation in various athletic activities, said eyewear being placed against the face of said wearer, said eyewear comprising:

a lens holding frame and a single 'wrap-around' shaped lens, said frame supporting said lens substantially in front of eye portion of said wearer, said frame and said lens defining an interior space, a single circumferential sealing means affixed to said frame and said lens for sealing said frame and said lens to the face of said wearer, the inner surface of said sealing means being contoured to fit the human face, the outer surface of said sealing means being contoured to fit within said frame and said lens, said sealing means including an inflatable and deflatable bladder, further including means for removing air from or introducing air into said bladder, whereby said bladder can be inflated or deflated, retaining means for holding said frame and said lens against the face of the wearer, wherein the improvement comprises the attachment of said sealing means to common 'wrap-around' eyewear, eliminating the need for a large or bulky frame for attachment purposes, also eliminating the need for an undesirable strap, whereby eyewear is provided that can be worn for a variety of athletic activities, said eyewear having said seal assembly not immediately apparent to the casual observer.

2. The eyewear of claim 1 wherein said sealing means is a foam rubber layer overlying a bladder.

3. The eyewear of claim 1 wherein said means for removing air from or introducing air into said bladder is a mouthpiece, whereby said wearer can "suck" air from or blow air into said bladder.

4. The eyewear of claim 1 wherein said means for removing air from and introducing air into said bladder is a pump mechanism, whereby air is pumped from or blown into said bladder.

5. The eyewear of claim 1 further including closeable ventilation means whereby when opened, air circulation is allowed into the interior portion of the glasses, and when closed, the ingress of water is prohibited.

6. The eyewear of claim 1 further including air removal means for removing air from the interior portion of said eyewear with connection means for connecting said interior portion to said air removal means, whereby upon using said air removal means, a slight vacuum is created, promoting a better seal with face of said wearer.

7. The eyewear of claim 1 wherein said lens is tinted, polarized and/or otherwise provided with means for filtering light e.g. the sun's rays.

8. The eyewear of claim 1 wherein said frame and said lens are formed of resiliently deformable material whereby said eyewear more easily conforms to and seals about the wearer's eyes.

9. The eyewear of claim 1 wherein said retaining means comprises one or more tubular members of a resilient, flexible material, adjustment means, and means for preventing disassembly of the retaining means.

10. The eyewear of claim 1 further including an antifog coating on said lens.

11. Improved eyewear for protecting the eyes of a wearer during participation in various athletic activities, said eyewear being placed against the face of said wearer, said eyewear comprising a lens holding frame and a single 'wrap-around' shaped lens, said frame supporting said lens substantially in front of eye portion of said wearer, said frame and said lens defining an interior space, a single circumferential sealing means affixed to said frame and said lens for sealing said frame and said lens to the face of said wearer, the inner surface of said sealing means being contoured to fit the human face, the outer surface of said sealing means being contoured to fit within said frame and said lens, retaining means for holding said frame and said lens against the face of the wearer, air removal means for removing air from the interior portion of said eyewear with connection means for connecting said interioir portion to said air removal means, whereby upon using said air removal means, a slight vacuum is created, promoting a better seal with face of said wearer, wherein said air removal means is a mouthpiece, whereby the wearer can "suck" air from wherein the improvement comprises the improved seal achieved by creating a slight vacuum in addition to the attachment of said sealing means to common 'wrap-around' eyewear, eliminating the need for a large or bulky frame for attachment purposes, also eliminating the need for an undesirable strap, whereby eyewear is provided that can be worn for a variety of athletic activities, said eyewear having said seal assembly not immediately apparent to the casual observer.

12. The eyewear of claim 11 wherein connection means comprises tubing.

13. The eyewear of claim 11 wherein said mouthpiece further includes a pump mechanism whereby air is pumped from said interior portion.

14. The eyewear of claim 11 further including closeable ventilation means wherein when opened, air circulation is allowed into the interior portion of the glasses, and when closed, the ingress of water is prohibited.

15. The eyewear of claim 11 wherein said sealing means includes an inflatable and deflatable bladder, further including means for removing air from and introducing air into said bladder, whereby said bladder can be inflated or deflated, 16. The eyewear of claim 11 wherein said sealing means is made of a foam rubber material.

17. Improved eyewear for protecting the eyes of a wearer during participation in various athletic activities, said eyewear being placed against the face of said wearer, said eyewear comprising a lens holding frame and a single 'wrap-around' shaped lens, said frame supporting said lens substantially in front of eye portion of said wearer, said frame and said lens defining an interior space, a single circumferential sealing means affixed to said frame and said lens for sealing said frame and said lens to the face of said wearer, the inner surface of said sealing means being contoured to fit the human face, the outer surface of said sealing means being contoured to fit within said frame and said lens, retaining means for holding said frame and said lens against the face of the wearer, further including closeable ventilation means whereby when opened, air circulation is allowed into the interior portion of the glasses, and when closed, the ingress of water is prohibited, wherein the improvement comprises closeable vents in addition to the attachment of said sealing means to common 'wrap-around' eyewear, eliminating the need for a large or bulky frame for attachment purposes, also eliminating the need for an undesirable strap, whereby eyewear is provided that can be worn for a variety of athletic activities, said eyewear having said seal assembly not immediately apparent to the casual observer.

18. The eyewear of claim 17 further including air removal means for removing air from the interior portion of said eyewear with connection means for connecting said interior portion to said air removal means, whereby upon using said air removal means, a slight vacuum is created, promoting a better seal with face of said wearer, 19. The eyewear of claim 17 wherein said sealing means includes an inflatable and deflatable bladder, further including means for removing air from or introducing air into said bladder, whereby said bladder can be inflated or deflated, 20. The eyewear of claim 17 wherein said sealing means is made of a foam rubber material.

* * * * *